US010786804B2

(12) United States Patent
Segawa et al.

(10) Patent No.: US 10,786,804 B2
(45) Date of Patent: Sep. 29, 2020

(54) METHOD FOR PRODUCING DEHYDROGENATION CATALYST, METHOD FOR PRODUCING UNSATURATED HYDROCARBON, AND METHOD FOR PRODUCING CONJUGATED DIENE

(71) Applicant: ENEOS Corporation, Tokyo (JP)

(72) Inventors: Atsushi Segawa, Tokyo (JP); Nobuhiro Kimura, Tokyo (JP)

(73) Assignee: ENEOS Corporation, Tokyo (JP)

( * ) Notice: Subject to any disclaimer, the term of this patent is extended or adjusted under 35 U.S.C. 154(b) by 0 days.

(21) Appl. No.: 16/093,329

(22) PCT Filed: Apr. 14, 2017

(86) PCT No.: PCT/JP2017/015317
§ 371 (c)(1),
(2) Date: Oct. 12, 2018

(87) PCT Pub. No.: WO2017/179708
PCT Pub. Date: Oct. 19, 2017

(65) Prior Publication Data
US 2019/0201874 A1 Jul. 4, 2019

(30) Foreign Application Priority Data
Apr. 15, 2016 (JP) ................. 2016-082119

(51) Int. Cl.
B01J 23/62 (2006.01)
B01J 35/00 (2006.01)
B01J 23/00 (2006.01)
B01J 37/02 (2006.01)
C07C 5/333 (2006.01)
C07C 11/08 (2006.01)
C07C 11/167 (2006.01)
B01J 21/04 (2006.01)
B01J 21/10 (2006.01)
B01J 37/08 (2006.01)

(52) U.S. Cl.
CPC ............ B01J 23/626 (2013.01); B01J 21/04 (2013.01); B01J 21/10 (2013.01); B01J 23/005 (2013.01); B01J 35/002 (2013.01); B01J 37/0201 (2013.01); B01J 37/0205 (2013.01); B01J 37/0213 (2013.01); B01J 37/0236 (2013.01); B01J 37/08 (2013.01); C07C 5/333 (2013.01); C07C 5/3337 (2013.01); C07C 11/08 (2013.01); C07C 11/167 (2013.01); C07C 2523/62 (2013.01)

(58) Field of Classification Search
CPC ........ B01J 23/626; B01J 23/42; B01J 23/462; B01J 23/468; B01J 2523/43; B01J 2523/821; B01J 2523/827; B01J 2523/828; C07C 5/333; C07C 5/3337; C07C 11/08; C07C 11/167; C07C 2523/62
USPC ........................ 502/325, 339, 349; 585/601
See application file for complete search history.

(56) References Cited

U.S. PATENT DOCUMENTS

| | | | | | |
|---|---|---|---|---|---|
| 3,576,766 | A | * | 4/1971 | Rausch et al. | B01J 23/6567 502/330 |
| 3,794,599 | A | * | 2/1974 | Dautzenberg et al. | B01J 23/56 502/334 |
| 4,469,811 | A | * | 9/1984 | Lucien | B01J 23/626 502/227 |
| 5,536,695 | A | * | 7/1996 | Blejean | B01J 23/02 502/327 |
| 2014/0309470 | A1 | * | 10/2014 | Park | B01J 23/626 585/660 |
| 2019/0263731 | A1 | * | 8/2019 | Araki | B01J 23/26 |

FOREIGN PATENT DOCUMENTS

| | | |
|---|---|---|
| JP | S47-009457 A | 5/1972 |
| JP | S57-140730 A | 8/1982 |
| JP | S59-012756 A | 1/1984 |
| JP | S60-001139 A | 1/1985 |
| JP | 2003-220335 A | 8/2003 |
| JP | 2014-205135 A | 10/2014 |

OTHER PUBLICATIONS

Japan Patent Office, International Search Report and Written Opinion issued in International Application No. PCT/JP2017/015317 (dated Jul. 18, 2018) 14 pp.
Japan Patent Office, International Preliminary Report on Patentability issued in International Application No. PCT/JP2017/015317 (dated Oct. 25, 2018) 11 pp.

* cited by examiner

Primary Examiner — Patricia L. Hailey
(74) Attorney, Agent, or Firm — Leydig, Voit & Mayer, Ltd.

(57) ABSTRACT

A method for producing a dehydrogenation catalyst, comprising: a step of impregnating a carrier with a first solution having a tin source dissolved therein, so as to have tin supported on the carrier; and a step of impregnating the carrier with a second solution having an active metal source dissolved therein, so as to have the active metal supported on the carrier, wherein the tin source is at least one selected from the group consisting of sodium stannate and potassium stannate, and the active metal source has at least one active metal selected from the group consisting of platinum, ruthenium and iridium, and has no chlorine atom.

4 Claims, No Drawings

METHOD FOR PRODUCING DEHYDROGENATION CATALYST, METHOD FOR PRODUCING UNSATURATED HYDROCARBON, AND METHOD FOR PRODUCING CONJUGATED DIENE

CROSS-REFERENCE TO RELATED APPLICATIONS

This patent application is the U.S. national phase of International Application No. PCT/JP2017/015317, filed on Apr. 14, 2017, which claims the benefit of Japanese Patent Application No. 2016-082119, filed Apr. 15, 2016, the disclosures of which are incorporated herein by reference in their entireties for all purposes.

TECHNICAL FIELD

The present invention relates to a method for producing a dehydrogenation catalyst, a method for producing an unsaturated hydrocarbon, and a method for producing a conjugated diene.

BACKGROUND ART

Because of motorization mainly in the recent Asia, the demand of conjugated dienes including butadiene as raw materials and the like for synthetic rubber is expected to increase. As methods for producing a conjugated diene, for example, a method for producing a conjugated diene by direct dehydrogenation of n-butane using a dehydrogenation catalyst (Patent Literature 1) and a method for producing a conjugated diene by oxidative dehydrogenation of n-butene (Patent Literatures 2 to 4) are known.

CITATION LIST

Patent Literature

Patent Literature 1: Japanese Unexamined Patent Publication No. 2014-205135
Patent Literature 2: Japanese Unexamined Patent Publication No. S57-140730
Patent Literature 3: Japanese Unexamined Patent Publication No. S60-1139
Patent Literature 4: Japanese Unexamined Patent Publication No. 2003-220335

SUMMARY OF INVENTION

Technical Problem

With the increasing demand of unsaturated hydrocarbons such as conjugated dienes, the development of various methods for producing unsaturated hydrocarbons, having different features such as required characteristics, operating costs, and reaction efficiency of manufacturing apparatuses is required.

An object of the present invention is to provide a method for producing a dehydrogenation catalyst, which can be suitably used for production of an unsaturated hydrocarbon. Another object of the present invention is to provide a method for producing an unsaturated hydrocarbon using the above dehydrogenation catalyst.

Solution to Problem

One aspect of the present invention relates to a method for producing a dehydrogenation catalyst. This production method comprises a step of impregnating a carrier with a first solution having a tin source dissolved therein, so as to have tin supported on the carrier, and a step of impregnating the carrier with a second solution having an active metal source dissolved therein, so as to have the active metal supported on the carrier. Further, in this production method, the tin source is at least one selected from the group consisting of sodium stannate and potassium stannate, and the active metal source has at least one active metal selected from the group consisting of platinum, ruthenium and iridium, and has no chlorine atom.

In such a production method, since both the tin source and the active metal source contain no chlorine atom, a dehydrogenation catalyst in which the content of a chlorine atom is extremely low or zero, is obtained. According to the findings of the present inventors, when a dehydrogenation catalyst contains a chlorine atom in a predetermined amount or more, hydrochloric acid is generated in a reaction where water coexists therewith, causing the corrosion of the reaction vessel. According to the above production method, a dehydrogenation catalyst can be obtained, which is capable of sufficiently suppressing the generation of hydrochloric acid and the resulting corrosion of the reaction vessel, even when applied to a reaction where water can coexist therewith.

Further, in the above production method, sodium stannate or potassium stannate is used as a tin source. Accordingly, the dispersion state of tin on the carrier becomes suitable as a dehydrogenation catalyst, and the dehydrogenation catalyst becomes excellent in reactivity, and less deteriorated.

In one embodiment, the first solution may be an aqueous solution. Sodium stannate and potassium stannate are both water soluble, and thus the first solution can be easily adjusted using water as a solvent. Further, with the use of water as a solvent, as compared with a case of using an organic solvent, the environmental load can be reduced and the cost can be limited, for example.

In one embodiment, the dehydrogenation catalyst may be a catalyst for dehydrogenation to obtain at least one unsaturated hydrocarbon selected from the group consisting of olefins and conjugated dienes from alkanes. The dehydrogenation catalyst produced by the above production method is excellent in ability of dehydrogenating an alkane, and thus can be suitably used as a dehydrogenation catalyst for obtaining an unsaturated hydrocarbon from the alkane.

In one embodiment, the dehydrogenation catalyst may be a catalyst for dehydrogenation to obtain a conjugated diene from olefins. The dehydrogenation catalyst produced by the above production method is excellent in ability of dehydrogenating olefins, and thus can be suitably used as a catalyst for dehydrogenation to obtain a conjugated diene from olefins.

Another aspect of the present invention relates to a method for producing an unsaturated hydrocarbon. The method for producing an unsaturated hydrocarbon comprises a step of performing dehydrogenation of an alkane using a dehydrogenation catalyst, so as to obtain at least one unsaturated hydrocarbon selected from the group consisting of olefins and conjugated dienes, wherein as the dehydrogenation catalyst, a dehydrogenation catalyst produced by the above method for producing a dehydrogenation catalyst is used.

In the method for producing an unsaturated hydrocarbon, a catalyst produced by the above production method is used as a dehydrogenation catalyst, so that the catalyst is excellent in reactivity and catalyst life in dehydrogenation, and an unsaturated hydrocarbon can be efficiently produced. Moreover, in the method for producing an unsaturated hydrocarbon, the chlorine content of the dehydrogenation catalyst is significantly low or zero and thus the generation of hydrochloric acid is suppressed, and the corrosion of the reaction vessel is sufficiently suppressed, even when water coexists therewith in dehydrogenation.

Yet another aspect of the present invention relates to a method for producing a conjugated diene. The method for producing a conjugated diene comprises a step of performing dehydrogenation of olefins using a dehydrogenation catalyst to obtain a conjugated diene, wherein a dehydrogenation catalyst produced by the above method for producing a dehydrogenation catalyst is used as a dehydrogenation catalyst.

In the method for producing a conjugated diene, a catalyst produced by the above production method is used as a dehydrogenation catalyst, so that the catalyst is excellent in reactivity and catalyst life in dehydrogenation, and thus a conjugated diene can be produced efficiently. Further, in the method for producing a conjugated diene, the chlorine content of the dehydrogenation catalyst is significantly low or zero, so that even when water coexists therewith in dehydrogenation, the generation of hydrochloric acid is suppressed, and the corrosion of the reaction vessel is sufficiently suppressed.

Advantageous Effects of Invention

According to the present invention, a method for producing a dehydrogenation catalyst, which can be suitably used in production of an unsaturated hydrocarbon, is provided. Furthermore, according to the present invention, a method for producing an unsaturated hydrocarbon using the above dehydrogenation catalyst is provided.

DESCRIPTION OF EMBODIMENTS

Hereinafter, suitable embodiments of the present invention are described. However, the invention is not intended to be limited to the following embodiments.

(Method for Producing Dehydrogenation Catalyst)

A method for producing a dehydrogenation catalyst according to the present embodiment comprises a step (tin supporting step) of impregnating a carrier with a first solution having a tin source dissolved therein, so as to have tin supported on the carrier, and a step (active metal supporting step) of impregnating the carrier with a second solution having an active metal source dissolved therein, so as to have the active metal supported on the carrier. In this embodiment, the tin source is at least one selected from the group consisting of sodium stannate and potassium stannate, and the active metal source has at least one active metal selected from the group consisting of platinum, ruthenium and iridium, and has no chlorine atom.

In this embodiment, both the tin source and the active metal source contain no chlorine atom, and thus a dehydrogenation catalyst in which the chlorine atom content is extremely low or zero can be obtained. Note that according to the findings of the present inventors, when the dehydrogenation catalyst contains a chlorine atom in a predetermined amount or more, hydrochloric acid is generated in a reaction where water coexists therewith, causing the corrosion of the reaction vessel. In this respect, by the use of the method for producing a dehydrogenation catalyst according to the embodiment, dehydrogenation catalyst capable of sufficiently suppressing the generation of hydrochloric acid and the resulting corrosion of the reaction vessel even when applied to the reaction where water can coexist therewith can be obtained.

In the method for producing a dehydrogenation catalyst according to this embodiment, sodium stannate or potassium stannate is used as a tin source. Accordingly, the dispersion state of tin on the carrier becomes suitable as a dehydrogenation catalyst, and thus the resulting dehydrogenation catalyst becomes excellent in reactivity, and less deteriorated.

Hereinafter, each step of the method for producing a dehydrogenation catalyst according to this embodiment will be described in detail.

<Tin Supporting Step>

The tin supporting step is a step of impregnating a carrier with a first solution having a tin source dissolved therein, so as to have tin supported on the carrier. The tin source is at least one selected from the group consisting of sodium stannate and potassium stannate.

The solvent in the first solution may be any solvent capable of dissolving the tin source, and it is preferable that it is water from a view point such that the environmental load and the cost can be reduced. In this embodiment, sodium stannate and potassium stannate as tin sources are water-soluble, and even a solvent in the first solution is water, the tin source can be easily dissolved therein. Further, in this embodiment, the tin source is sodium stannate or potassium stannate, and thus even when water is used as a solvent in the first solution, tin can be supported on the carrier with good dispersibility.

The pH of the first solution may range from 8 to 14, and preferably ranges from 10 to 13. In this embodiment, the tin source is sodium stannate or potassium stannate, and thus can be stably present in a dissolved state in the solution with such a pH. Note that, the tin source is dissolved in water, and thus the pH of the above range can be achieved. That is, in this embodiment, adding an acid, a base or the like is not required for preparation of the first solution, and the first solution can be easily prepared only by dissolving the tin source in water.

The amount of the tin source blended in the first solution can be adjusted as appropriate according to the amount of tin to be supported on the carrier, the supporting method, and the like. For example, the tin atom content of the first solution may be 0.01 mass % or more, and 0.1 mass % or more. Also, the tin atom content of the first solution may be 20 mass % or less, and 10 mass % or less.

In the tin supporting step, a carrier is impregnated with the first solution, so as to have tin supported on the carrier. Impregnation of the carrier with the first solution may be performed while, for example, removing a solvent of the first solution using an evaporator or the like.

Furthermore, the carrier after impregnation may be dried and calcined. Drying conditions can be appropriately selected depending on the solvent of the first solution. The calcination temperature may range from, for example, 300 to 900° C., preferably ranges from 400 to 800° C. The calcination time may range from, for example, 1 to 10 hours, and preferably ranges from 2 to 5 hours.

It is preferable that the carrier is an inorganic oxide carrier. Examples of such an inorganic oxide carrier include carriers containing inorganic oxides, such as alumina, alumina magnesia, magnesia, titania, silica, silica-alumina, silica magnesia, ferrite, spinel type structures (magnesium spinel, iron spinel, zinc spinel, and manganese spinel).

It is preferable that the carrier is a carrier, containing aluminum (Al). The Al content of the carrier may be 25 mass % or more and it is preferable that it is 50 mass % or more based on the total mass of the carrier.

It is preferable that the carrier is a spinel-type structural body having a spinel structure, such as a magnesium spinel ($MgAl_2O_4$). Thus, the acidity of the carrier is decreased, by which an effect of suppressing carbon deposition is exerted.

In this embodiment, after having tin supported on a carrier in the tin supporting step, an active metal may be supported on the carrier in the active metal supporting step described later. Furthermore, after having an active metal supported on a carrier in the active metal supporting step described later, tin may be supported on the carrier in the tin supporting step.

<Active Metal Supporting Step>

The active metal supporting step is a step of impregnating a carrier with a second solution containing an active metal source, so as to have the active metal supported on the carrier. The active metal is at least one selected from the group consisting of platinum, ruthenium and iridium. Also, the active metal source has at least one active metal selected from the group consisting of platinum, ruthenium and iridium, and, has no chlorine atom.

The active metal source can also be at least one selected from the group consisting of a platinum source, a ruthenium source and an iridium source. The platinum source, the ruthenium source and the iridium source have no chlorine atom.

The platinum source may be a compound having platinum (Pt), but having no chlorine atom. Examples of the platinum source include tetraammineplatinum (II) acid, tetraammineplatinum (II) acid salt (e.g., nitrate), tetraammineplatinum (II) acid hydroxide solution, dinitrodiammineplatinum (II) nitric acid solution, hexahydroxoplatinum (IV) acid nitric acid solution, and hexahydroxoplatinum (IV) acid ethanolamine solution.

The ruthenium source may be a compound having ruthenium (Ru), but having no chlorine atom. Examples of the ruthenium source include ruthenium nitrate (III), sodium ruthenate (IV), and potassium ruthenate (IV).

The iridium source may be a compound having iridium (Ir), but having no chlorine atom. Examples of the iridium source include iridium nitrate (IV), and hexaammineiridium (III) hydroxide solution.

The solvent in the second solution may be any solvent capable of dissolving an active metal source. The solvent in the second solution may be water or ethanol, for example.

The amount of the active metal source blended in the second solution may be adjusted as appropriate according to the amount of an active metal supported on the carrier, a method for supporting and the like. For example, the content of the active metal in the second solution may be 0.01 mass % or more, and 0.1 mass % or more. Moreover, the content of the active metal in the second solution may be 10 mass % or less and 5 mass % or less.

In the active metal supporting step, a carrier is impregnated with a second solution, so as to have the active metal supported on the carrier. Impregnation of the carrier with the second solution may be performed while removing a solvent of the second solution using an evaporator, for example.

Furthermore, the carrier after impregnation may be dried and calcined. Drying conditions can be appropriately selected depending on the solvent of the second solution. The calcination temperature may range from, for example, 200 to 700° C., and preferably ranges from 300 to 600° C. The calcination time may range from, for example, 1 to 10 hours, and preferably ranges from 2 to 5 hours. Note that when the active metal contains ruthenium, it is preferable that calcination is carried out under a nitrogen stream.

In this embodiment, after having tin supported on a carrier in the above tin supporting step, an active metal may be supported on the carrier in the active metal supporting step. Furthermore, after having an active metal supported on a carrier in the active metal supporting step, tin may be supported on the carrier in the above tin supporting step.

A dehydrogenation catalyst produced by the method for producing a dehydrogenation catalyst according to the embodiment contains a carrier, tin supported on the carrier, and at least one active metal selected from the group consisting of platinum, ruthenium and iridium supported on the carrier.

The dehydrogenation catalyst can be suitably used as a catalyst for dehydrogenation using an alkane as a raw material. Through the dehydrogenation, at least one unsaturated hydrocarbon selected from the group consisting of olefins and conjugated dienes is obtained from the alkane.

Moreover, the dehydrogenation catalyst can be suitably used as a catalyst for dehydrogenation using an olefin as a raw material. Through the dehydrogenation, a conjugated diene is obtained from the olefins.

When the dehydrogenation catalyst is used for dehydrogenation using an alkane as a raw material, the amount of tin supported in the dehydrogenation catalyst may be, for example, 1 mass % or more, and it is preferable that it is 1.3 mass % or more, may be 9 mass % or less, and it is preferable that it is 7 mass % or less based on the total mass of the dehydrogenation catalyst. With such an amount of tin supported, the resulting dehydrogenation ability in dehydrogenation using an alkane as a raw material is improved, as well as the coke deposition is suppressed in the dehydrogenation so as to be able to prolong the life of the catalyst.

When the dehydrogenation catalyst is used for dehydrogenation using an olefin as a raw material, the amount of tin supported in the dehydrogenation catalyst may be, for example, 5 mass % or more, and it is preferable that it is 7 mass % or more, may be 25 mass % or less, and it is preferable that it is 18 mass % or less based on the total mass of the dehydrogenation catalyst. With such an amount of tin supported, the dehydrogenation ability in the dehydrogenation using an olefin as a raw material is improved, as well as the coke deposition in the dehydrogenation is suppressed, so as to be able to prolong the life of the catalyst.

The amount of the active metal supported in the dehydrogenation catalyst may be, for example, 0.1 mass % or more, and it is preferable that it is 0.5 mass % or more based on the total mass of the dehydrogenation catalyst. Thus the catalytic activity of the dehydrogenation catalyst is further improved. Moreover, the amount of the active metal supported in the dehydrogenation catalyst may be, for example, 5 mass % or less, and it is preferable that it is 2 mass % or less based on the total mass of the dehydrogenation catalyst. This tends to improve the dispersibility of the active metal in the dehydrogenation catalyst, and the activity per amount supported.

Note that the amount of tin and the amount of an active metal supported in the dehydrogenation catalyst can be measured by emission spectroscopy using inductively coupled plasma (ICP) as a light source. In the measurement, a sample solution is atomized and then introduced into Ar plasma, the light, which is emitted when an excited element returns to its ground state, is dispersed, the element is qualitatively analyzed based on the wavelength, and thus it is determined from the intensity.

In the dehydrogenation catalyst, the active metal and tin may interact with each other to form an alloy, for example. Accordingly, the dehydrogenation catalyst tends to have improved durability.

The dehydrogenation catalyst can be suitably used as described above as a catalyst for dehydrogenation using an alkane as a raw material, or, as a catalyst for dehydrogenation using an olefin as a raw material. In addition, the dehydrogenation catalyst may be used in applications other than them, for example, as a catalyst for dehydrogenation of oxygen-containing compounds such as alcohol, aldehyde, ketone, and carboxylic acid, a catalyst for hydrogenation that is a reverse reaction of dehydrogenation.

The dehydrogenation catalyst may be used in a reaction after subjected to reduction treatment. Reduction treatment can be performed by keeping the dehydrogenation catalyst at 40 to 600° C. under a reducing gas atmosphere, for example. The retention time may range from 0.05 to 24 hours, for example. Reducing gas may be hydrogen, carbon monoxide, or the like.

(Method for Producing Unsaturated Hydrocarbon)

The method for producing an unsaturated hydrocarbon according to this embodiment comprises a step (dehydrogenation step) of performing dehydrogenation of an alkane using a dehydrogenation catalyst, so as to obtain at least one unsaturated hydrocarbon selected from the group consisting of olefins and conjugated dienes. The dehydrogenation catalyst is a dehydrogenation catalyst produced by the above production method.

The dehydrogenation step may be a step of bringing a raw-material gas containing an alkane into contact with the dehydrogenation catalyst, so as to obtain a product gas containing an unsaturated hydrocarbon, for example.

The number of carbon atoms in the alkane may be the same as the number of carbon atoms in an unsaturated hydrocarbon of interest. Specifically, the alkane may be a saturated hydrocarbon obtained upon hydrogenation of double bonds existing in the unsaturated hydrocarbon of interest. The number of carbon atoms in the alkane may range from, for example, 3 to 10 and 3 to 6.

Alkanes may be, for example, chain or cyclic alkanes. Examples of chain alkanes include propane, butane, pentane, hexane, heptane, octane, and decane. More specifically, examples of linear alkanes include n-butane, n-pentane, n-hexane, n-heptane, n-octane, and n-decane. Examples of branched alkanes include isobutane, isopentane, 2-methylpentane, 3-methylpentane, 2,3-dimethylpentane, isoheptane, isooctane, and isodecane. Examples of cyclic alkanes include cyclopentane, cyclohexane, cycloheptane, cyclooctane, cyclodecane, and methyl cyclohexane. The raw-material gas may be a gas containing one alkane, or may be a gas containing two or more alkanes.

In the raw-material gas, the partial pressure of the alkane may be 1.0 MPa or less, 0.1 MPa or less, and 0.01 MPa or less. Decreasing the alkane partial pressure in the raw material gas facilitates further improvement of the conversion rate of the alkane.

Moreover, it is preferable that the alkane partial pressure in the raw-material gas is 0.001 MPa or more, and is more preferable that it is 0.005 MPa or more in view of reducing the reactor size relative to the flow rate of the raw material.

The raw-material gas may further contain an inert gas such as nitrogen and argon. Furthermore, the raw-material gas may further contain steam.

When the raw-material gas contains steam, it is preferable that the content of the steam is 1 times by mole or more, and is more preferable that it is 1.5 times by mole or more than that of the alkane. The raw material gas containing steam may result in a case where a decrease in the activity of the catalyst is suppressed. In addition, the steam content may be 50 times by mole or less, and preferably 10 times by mole or less than that of the alkane, for example.

The raw-material gas may further contain other components such as hydrogen, oxygen, carbon monoxide, carbonic acid gas, olefins, dimes, and the like in addition to the above components.

In this embodiment, the product gas contains at least one unsaturated hydrocarbon selected from the group consisting of olefins and conjugated dienes. The number of carbon atoms of an olefin and that of a conjugated diene may be the same as the number of carbon atoms of the alkane, and may range from, for example, 4 to 10 and 4 to 6.

Examples of olefins include butene, pentene, hexene, heptene, octene, nonene, and decene or may be any isomer thereof. Examples of the conjugated diene include 1,3-butadiene, 1,3-pentadiene, isoprene, 1,3-hexadiene, 1,3-heptadiene, 1,3-octadiene, 1,3-nonadiene, and 1,3-decadiene. The product gas may be a gas containing one unsaturated hydrocarbon or a gas containing two or more unsaturated hydrocarbons. For example, the product gas may be a gas containing an olefin and a conjugated diene.

The dehydrogenation step may be carried out by using the reactor filled with a dehydrogenation catalyst, and causing a raw-material gas to flow in the reactor, for example. As the reactor, various reactors to be used for a gas phase reaction using a solid catalyst can be used. Examples of the reactor include a fixed bed reactor, a radial flow reactor, and a tubular reactor.

The reaction mode of dehydrogenation may be a fixed-bed mode, a moving-bed mode, or a fluidized-bed mode, for example. Among these, a fixed-bed mode is preferred in view of facility cost.

The reaction temperature for dehydrogenation; that is, the temperature within a reactor may range from 300 to 800° C. and 500 to 700° C. in view of reaction efficiency. If the reaction temperature is 500° C. or higher, the amount of an unsaturated hydrocarbon to be generated is likely to further increase. If the reaction temperature is 700° C. or lower, high activity is likely to be maintained over a long period of time.

Reaction pressure, i.e. pressure in a reactor may range from 0.01 to 1 MPa, 0.05 to 0.8 MPa, and 0.1 to 0.5 MPa. The reaction pressure within the above range makes dehydrogenation to proceed more easily, and thus even better reaction efficiency is likely to be obtained.

When the dehydrogenation step is performed in a continuous reaction mode of continuously feeding a raw-material gas, the weigh hourly space velocity (hereinafter, referred to as "WHSV") may be 0.1 $h^{-1}$ or more, 1.0 $h^{-1}$ or more, 100 $h^{-1}$ or less, and 30 $h^{-1}$ or less. Here, the term "WHSV" refers to the ratio (F/W) of F, the feed rate (amount fed/time) of the raw-material gas, to W, the mass of the dehydrogenation catalyst in a continuous reaction apparatus. Note that the further preferable ranges of amounts of the raw-material gas and the catalyst to be used may be selected as appropriate according to the reaction conditions, the activity of the catalyst, and the like, and WHSV is not limited to the above range.

The dehydrogenation step may further comprise filling the reactor with a catalyst other than the dehydrogenation catalyst (hereinafter, also referred to as a first dehydrogenation catalyst) according to the embodiment.

For example, in this embodiment, subsequent to filling a reactor with the first dehydrogenation catalyst, the reactor may be further filled with a second dehydrogenation catalyst for catalyzing dehydrogenation of olefins into conjugated dienes. The first dehydrogenation catalyst is excellent in reaction activity of the dehydrogenation of alkanes into olefins, so that filling with the second dehydrogenation catalyst subsequent to filling with the first dehydrogenation catalyst can increase the proportion of the conjugated dienes in the thus obtained product gas.

The production method according to this embodiment may further comprise a step of bringing a product gas (hereinafter, also referred to as a first: product gas) containing olefins obtained in the dehydrogenation step into contact with the second dehydrogenation catalyst to perform dehydrogenation of the olefins, so as to obtain a second product gas containing conjugated dienes. According to such a production method, it is possible to obtain a product gas containing a higher amount of the conjugated dienes.

As the second dehydrogenation catalyst, any catalyst can be used without particular limitation, as long as it is a catalyst for dehydrogenation of olefins. For example, as the second dehydrogenation catalyst, a noble metal catalyst, a catalyst containing Fe and K, and a catalyst containing Mo or the like, can be used, for example. Furthermore, as the second dehydrogenation catalyst, a dehydrogenation catalyst produced by the method for producing a dehydrogenation catalyst according to the embodiment may also be used.

(Method for Producing Conjugated Diene)

The method for producing a conjugated diene according to the embodiment comprises a step (dehydrogenation step) of performing dehydrogenation of olefins using a dehydrogenation catalyst, so as to obtain conjugated dienes. The dehydrogenation catalyst is a dehydrogenation catalyst produced by the above-described production method.

The dehydrogenation step may be a step of bringing a raw-material gas containing olefins into contact with a dehydrogenation catalyst, so as to obtain a product gas containing conjugated dienes, for example.

The number of carbon atoms of an olefin may be the same as the number of carbon atoms of a conjugated diene of interest. Specifically, the olefin may be a hydrocarbon compound obtained when one of the double bonds existing in a conjugated diene of interest is hydrogenated. The number of carbon atoms of the olefins may range from, for example, 4 to 10 and 4 to 6.

Olefins may be, for example, chain or cyclic olefins. Chain olefins may be of at least one selected from the group consisting of butene, pentene, hexene, heptene, octene, nonene and decene, for example. Chain olefins may be linear or branched. Linear olefins may be of, for example, at least one selected from the group consisting of n-butene, n-pentene, n-hexene, n-heptene, n-octene, n-nonene and n-decene. Branched olefins may be of, for example, at least one selected from the group consisting of isopentene, 2-methylpentene, 3-methylpentene, 2,3-dimethyl-pentene, isoheptene, isooctene, isononen and isodecene. The raw-material gas may be a gas containing one of the above olefins alone, or may be a gas containing two or more thereof.

In the raw-material gas, the partial pressure of olefins may be 1.0 MPa or less, 0.1 MPa or less, and 0.01 MPa or less. Decreasing the partial pressure of olefins in the raw-material gas facilitates the further improvement of the conversion rate of the olefins.

Also, it is preferable that the partial pressure of olefin in the raw-material gas is 0.001 MPa or more, and is more preferable that it is 0.005 MPa or more in view of reducing the reactor size relative to the flow rate of the raw material.

The raw-material gas may further contain an inert gas such as nitrogen and argon, and may further contain steam.

When the raw-material gas contains steam, it is preferable that the steam content is 1.0 times by mole or more, and is more preferable that it is 1.5 times by mole or more, than that of olefins. The raw-material gas containing steam may result in a case where a decrease in the activity of the catalyst is more significantly suppressed. The steam content may be, for example, 50 times by mole or less, and preferably 10 times by mole or less, than that of olefins.

The raw-material gas may further contain other components such as hydrogen, oxygen, carbon monoxide, carbonic acid gas, alkanes, and dienes, in addition to the above components.

Examples of the conjugated diene obtained by the dehydrogenation step include butadiene (1,3-butadiene), 1,3-pentadiene, isoprene, 1,3-hexadiene, 1,3-heptadiene, 1,3-octadiene, 1,3-nonadiene, and 1,3-decadiene. The product gas may be a gas containing one conjugated diene or a gas containing two or more conjugated dienes.

The dehydrogenation step may be carried out by using the reactor filled with a dehydrogenation catalyst, and causing a raw-material gas to flow in the reactor. As the reactor, various reactors to be used for gas phase reaction using a solid catalyst can be used. Examples of the reactor include a fixed-bed adiabatic reactor, a radial flow reactor, and a tubular reactor.

The reaction mode of dehydrogenation may be, for example, a fixed-bed mode, a moving-bed mode, or a fluidized-bed mode. Of these, a fixed bed mode is preferred in view of facility cost.

The reaction temperature for dehydrogenation; that is, the temperature in the reactor may range from 300 to 800° C., 400 to 700° C., and 500 to 650° C. in view of reaction efficiency. The reaction temperature of 300° C. or higher does not result in an excessive decrease in the equilibrium conversion rate of olefins, and thus the yield of the conjugated diene tends to be further improved. The reaction temperature of 800° C. or lower does not result in an excessively increased coking rate, and thus the high activity of the dehydrogenation catalyst is likely to be maintained over a longer period of time.

The reaction pressure, i.e. pressure in a reactor may range from 0.01 to 1 MPa, 0.05 to 0.8 MPa, and 0.1 to 0.5 MPa. The reaction pressure within the above range allows dehydrogenation to proceed more easily, and even better reaction efficiency is likely to be obtained.

When the dehydrogenation step is performed in a continuous reaction mode of continuously feeding a raw-material gas, WHSV may be, for example, 0.1 $h^{-1}$ or more, and 0.5 $h^{-1}$ or more. Furthermore, WHSV may be 20 $h^{-1}$ or less, and 10 $h^{-1}$ or less. Here, WHSV refers to the ratio (F/W) of F, the feed rate (amount fed/time) of the raw-material gas to W, the mass of the dehydrogenation catalyst. If WHSV is 0.1 $h^{-1}$ or more, the reactor size can be further reduced. If WHSV is 20 $h^{-1}$ or less, the conversion rate of olefins can be more increased. Note that the further preferable ranges of the amount of the raw-material gas and that of the catalyst to be used may be selected as appropriate according to the reaction conditions and the activity of the catalyst, for example, and WHSV is not limited to the above range.

The dehydrogenation step may further comprise filling a reactor with a catalyst other than the dehydrogenation catalyst (hereinafter, also referred to as a first dehydrogenation catalyst) according to the embodiment.

For example, in this embodiment, prior to filling of a reactor with the first dehydrogenation catalyst, the reactor is further filled with a solid catalyst (hereinafter, also referred to as "a second dehydrogenation catalyst") for catalyzing the dehydrogenation of alkanes into olefins, so that a raw-material gas can be obtained in the reactor. In other words, the dehydrogenation step may be carried out by using the reactor filled with the first and the second dehydrogenation catalysts, and causing a gas containing alkanes to flow in the reactor. Moreover, the dehydrogenation step may be carried out by causing a gas containing alkanes to flow in a reactor filled with the second dehydrogenation catalyst, and then in a reactor filled with the first dehydrogenation catalyst, in sequence.

As the second dehydrogenation catalyst, any catalyst can be used without particular limitation, as long as it is a catalyst for dehydrogenation of alkanes. For example, as the second dehydrogenation catalyst, a chromic acid/alumina catalyst, a nickel calcium phosphate catalyst, an iron chromium catalyst, and a chromium alumina magnesia catalyst can be used, for example. As the second dehydrogenation catalyst, a dehydrogenation catalyst produced by the method for producing a dehydrogenation catalyst according to the embodiment: may also be used.

Suitable embodiments of the present invention are described above, but the present invention is not limited to these embodiments.

Hereinafter, the present invention will be more specifically described with reference to Examples, but the present invention is not limited to Examples.

Example 1

20.0 g of commercially available γ-alumina (produced by Mizusawa Industrial Chemicals, Ltd. Neobead GB-13) was mixed with an aqueous solution having 11.8 g of sodium stannate (produced by Showa Kako Corporation, $Na_2SnO_3.3H_2O$) dissolved in about 240 ml of water, and then water was removed using an evaporator at about 50° C. Subsequently, the resultant was dried overnight at 130° C., and then calcined for 3 hours at 550° C.

Then, an aqueous solution of tetraammineplatinum (II) nitrate (produced by Tanaka Kikinzoku Kogyo, [Pt(NH$_3$)$_4$](NO$_3$)$_2$) was used for impregnating and supporting platinum, so that the amount of platinum supported was about 1 mass %. The resultant was dried overnight at 130° C., and then calcined at 550° C. for 3 hours, thereby obtaining a dehydrogenation catalyst A-1.

The thus obtained dehydrogenation catalyst A-1 was analyzed by emission spectrochemical analysis using inductively coupled plasma (ICP) (hereinafter, may also be referred to as ICP method) as a light source. As a result, the amount of Pt supported was 0.94 mass % and the amount of Sn supported was 15 mass %.

Example 2

A dehydrogenation catalyst A-2 was prepared in the same manner as in Example 1 except for using a nitric acid solution of dinitrodiammine platinum (II) instead of the aqueous solution of tetraammineplatinum (II) nitrate. The thus obtained dehydrogenation catalyst A-2 was analyzed by the ICP method, so that the amount of Pt supported was 1.02 mass %, and the amount of Sn supported was 15 mass %.

Example 3

A dehydrogenation catalyst A-3 was prepared in the same manner as in Example 1 except for using an aqueous solution of iridium nitrate (produced by FURUYA METAL Co., Ltd., Ir(NO$_3$)$_4$, Ir: 8.4 mass %) instead of the aqueous solution of tetraammineplatinum (II) nitrate. The thus obtained dehydrogenation catalyst A-3 was analyzed by the ICP method, so that the amount of Ir supported was 0.95 mass %, and the amount of Sn supported was 9.7 mass %.

Example 4

A dehydrogenation catalyst A-4 was prepared in the same manner as in Example 1 except for using an aqueous solution of ruthenium nitrate (produced by FURUYA METAL Co., Ltd., Ru(NO$_3$)$_3$, Ru: 4.5 mass %) instead of the aqueous solution of tetraammineplatinum (II) nitrate. The thus obtained dehydrogenation catalyst A-4 was analyzed by the ICP method, so that the amount of Ru supported was 0.91 mass %, and the amount of Sn supported was 9.5 mass %.

Example 5

20.0 g commercially available γ-alumina (produced by Mizusawa Industrial Chemicals Ltd., Neobead GB-13) was mixed with an aqueous solution having 25.1 g of magnesium nitrate hexahydrate (produced by Wako Pure Chemical Industries, Ltd., Mg(NO$_3$)$_2$.6H$_2$O) dissolved in water (about 150 ml), and then water was removed using an evaporator at about 50° C. Subsequently, the resultant was dried overnight at 130° C., calcined at 550° C. for 3 hours, and then continuously calcined at 800° C. for 3 hours. The obtained calcined product was mixed with an aqueous solution having 25.1 g of magnesium nitrate hexahydrate (produced by Wako Pure Chemical Industries, Ltd., Mg(NO$_3$)$_2$.6H$_2$O) dissolved in water (about 150 ml), and then water was removed using an evaporator at about 50° C. Subsequently, the resultant was dried overnight at 130° C., calcined at 550° C. for 3 hours, and then continuously calcined at 800° C. for 3 hours, thereby obtaining an alumina-magnesia carrier having a spinel structure. In addition, the obtained alumina-magnesia carrier was subjected to X-ray diffraction measurement, and thus diffraction peaks derived from Mg spinel were confirmed at 2θ=36.9, 44.8, 59.4, 65.3 deg.

10.0 g of the alumina-magnesia carrier was mixed with an aqueous solution having 3.7 g of sodium stannate (produced by Showa Kako Corporation, Na$_2$SnO$_3$.3H$_2$O) dissolved in about 100 ml of water, and then water was removed using an evaporator at about 50° C. The resultant was then dried overnight at 130° C., and then calcined at 550° C. for 3 hours.

A nitric acid solution of dinitrodiammine platinum (II) (produced by Tanaka Kikinzoku Kogyo, [Pt(NH$_3$)$_2$(NO$_2$)$_2$]/HNO$_3$) was used for impregnating and supporting platinum, so that the amount of platinum supported was about 1 mass %. The resultant was dried overnight at 130° C., and then calcined at 550° C. for 3 hours, thereby obtaining a dehydrogenation catalyst A-5.

The thus obtained dehydrogenation catalyst A-5 was analyzed by the ICP method, so that the amount of Pt supported was 0.90 mass and the amount of Sn supported was 8.1 mass %.

Example 6

An alumina-magnesia carrier was prepared in the same manner as in Example 5.

With 10.0 g of the thus obtained alumina-magnesia carrier, platinum was impregnated and supported using a nitric acid solution of dinitrodiammine platinum (II) (produced by Tanaka Kikinzoku Kogyo, [Pt(NH$_3$)$_2$(NO$_2$)$_2$]/HNO$_3$) so that the amount of platinum supported was about 1 mass %. The resultant was dried overnight at 130° C. and then calcified at 550° C. for 3 hours.

Subsequently, the resultant was mixed with an aqueous solution having 0.41 g of sodium stannate (produced by Showa Kako Corporation, $Na_2SnO_3 \cdot 3H_2O$) dissolved in about 6 ml of water, and then the mixture was subjected to an impregnation method to cause the carrier to support. The resultant was then dried overnight at 130° C., and then calcined at 550° C. for 3 hours, thereby obtaining a dehydrogenation catalyst A-6.

The thus obtained dehydrogenation catalyst A-6 was analyzed by the ICP method, so that the amount of Pt supported was 0.92 mass %, and the amount of Sn supported was 1.5 mass %.

Example 7

An alumina-magnesia carrier was prepared in the same manner as in Example 5.

with 10.0 g of the thus obtained alumina-magnesia carrier, platinum was impregnated and supported using a nitric acid solution of dinitrodiammine platinum (II) (produced by Tanaka Kikinzoku Kogyo, $[Pt(NH_3)_2(NO_2)_2]/HNO_3$), so that the amount of platinum supported was about 1 mass %. The resultant was dried overnight at 130° C. and then calcined at 550° C. for 3 hours.

Subsequently, the resultant was mixed with an aqueous solution having 0.62 g of sodium stannate (produced by Showa Kako Corporation, $Na_2SnO_3 \cdot 3H_2O$) dissolved in about 6 ml of water, and then the mixture was subjected to an impregnation method to cause the carrier to support. The resultant was then dried overnight at 130° C. and then calcined at 550° C. for 3 hours, thereby obtaining a dehydrogenation catalyst A-7.

The thus obtained dehydrogenation catalyst A-7 was analyzed by the ICP method, so that the amount of Pt supported was 0.87 mass %, and the amount of Sn supported was 2.2 mass %.

Example 8

An alumina-magnesia carrier was prepared in the same manner as in Example 5.

With 10.0 g of the thus obtained alumina-magnesia carrier, platinum was impregnated and supported using a nitric acid solution of dinitrodiammine platinum (II) (produced by Tanaka Kikinzoku Kogyo, $[Pt(NH_3)_2(NO_2)_2]/HNO_3$) so that the amount of platinum supported was about 1 mass %. The resultant was dried overnight at 130° C. and then calcined at 550° C. for 3 hours.

Subsequently, the resultant was mixed with an aqueous solution having 0.62 g of sodium stannate (produced by Showa Kako Corporation, $Na_2SnO_3 \cdot 3H_2O$) dissolved in about 30 ml of water, and then water was removed using an evaporator at about 50° C. The resultant was then dried overnight at 130° C., and then calcined at 550° C. for 3 hours, thereby obtaining a dehydrogenation catalyst A-8.

The thus obtained dehydrogenation catalyst A-8 was analyzed by the ICP method, so that the amount of Pt supported was 0.86 mass %, and the amount of Sn supported was 2.2 mass %.

Example 9

An alumina-magnesia carrier was prepared in the same manner as in Example 5.

With 10.0 g of the thus obtained alumina-magnesia carrier, platinum was impregnated and supported using a nitric acid solution of dinitrodiammine platinum (II) (produced by Tanaka Kikinzoku Kogyo, $[Pt(NH_3)_2(NO_2)_2]/HNO_3$) so that the amount of platinum supported was about 1 mass %. The resultant was dried overnight at 130° C. and then calcined at 550° C. for 3 hours.

Subsequently, the resultant was mixed with an aqueous solution having 0.82 g of sodium stannate (produced by Showa Kako Corporation, $Na_2SnO_3 \cdot 3H_2O$) dissolved in about 30 ml of water, and then water was removed using an evaporator at about 50° C. The resultant was then dried overnight at 130° C., and then calcined at 550° C. for 3 hours, thereby obtaining a dehydrogenation catalyst A-9.

The thus obtained dehydrogenation catalyst A-9 was analyzed by the ICP method, so that the amount of Pt supported was 0.92 mass %, and the amount of Sn supported was 3.0 mass %.

Example 10

10.0 g of commercially available γ-alumina (produced by Mizusawa Industrial Chemicals Ltd., Neobead GB-13) was mixed with an aqueous solution having 1.65 g of sodium stannate (produced by Showa Kako Corporation, $Na_2SnO_3 \cdot 3H_2O$) dissolved in about 50 ml of water, and then water was removed using an evaporator at about 50° C. The resultant was then dried overnight at 130° C. and then calcined at 550° C. for 3 hours.

Subsequently, platinum was impregnated and supported using a nitric acid solution of dinitrodiammine platinum (II) (produced by Tanaka Kikinzoka Kogyo, $[Pt(NH3)_2(NO_2)_2]/HNO_3$), so that the amount of platinum supported was about 1 mass %. The resultant was dried overnight at 130° C., and then calcined at 550° C. for 3 hours, thereby obtaining a dehydrogenation catalyst A-10.

The thus obtained dehydrogenation catalyst A-10 was analyzed by the ICP method, so that the amount of Pt supported was 0.90 mass %, and the amount of Sn supported was 6.7 mass %.

Comparative Example 1

A dehydrogenation catalyst B-1 was prepared in the same manner as in Example 1, except for using an aqueous solution having 10.0 g of tin sulfate (produced by Kishida Chemical Co., Ltd., $SnSO_4$) dissolved in about 200 ml of water instead of an aqueous sodium stannate solution. The thus obtained dehydrogenation catalyst B-1 was analyzed by the ICP method, so that the amount of Pt supported was 0.87 mass %, and the amount of Sn supported was 15 mass %.

Comparative Example 2

A dehydrogenation catalyst B-2 was prepared in the same manner as in Example 1, except for using an aqueous solution having 10.0 g of tin sulfate (produced by Kishida Chemical Co., Ltd., $SnSO_4$) dissolved in about 200 ml of water instead of an aqueous sodium tin solution, and using an ethanol amine solution of hexahydroxoplatinum (IV) acid instead of an aqueous solution of tetraammineplatinum (II) nitrate. The thus obtained dehydrogenation catalyst B-2 was analyzed by the ICP method, so that the amount of Pt supported was 0.88 mass %, and the amount of Sn supported was 15 mass %.

Comparative Example 3

An alumina-magnesia carrier was prepared the same manner as in Example 5.

With 10.0 g of thus obtained alumina-magnesia carrier, platinum was impregnated and supported using a nitric acid solution of dinitrodiammine platinum (II) (produced by Tanaka Kikinzoku Kogyo, [Pt(NH$_3$)$_2$(NO$_2$)$_2$]/HNO$_3$) so that the amount of platinum supported was about 1 mass %. The resultant was dried overnight at 130° C., and then calcined at 550° C. for 3 hours.

Subsequently, the resultant was mixed with an aqueous solution having 0.52 g of tin sulfate (produced by Kishida Chemical Co., Ltd., SnSO$_4$) dissolved in an about 6 ml of water and then subjected to an impregnation method to cause the carrier to support. The resultant was then dried overnight at 130° C., and then calcined at 550° C. for 3 hours, thereby obtaining a dehydrogenation catalyst B-3.

The thus obtained dehydrogenation catalyst B-3 was analyzed by the ICP method, so that the amount of Pt supported was 0.90 mass %, and the amount of Sn supported was 2.2 mass %.

Comparative Example 4

When tin acetate (produced by Aldrich, C$_4$H$_6$O$_4$Sn) was used instead of sodium stannate, tin acetate was not sufficiently dissolved in water, and thus catalyst preparation became difficult.

Comparative Example 5

When metastannic acid (produced by Showa Kako Corporation, H$_2$SnO$_3$) was used instead of sodium stannate, metastannic acid was not sufficiently dissolved in water, and thus catalyst preparation became difficult.

<Dehydrogenation 1>

Dehydrogenation was performed by the following method using the dehydrogenation catalysts obtained in Examples 1 to 5 and Comparative Examples 1 to 2.

A flow-type reactor having an inner diameter of 10 mmφ was filled with 1.00 g of the dehydrogenation catalyst, hydrogen reduction was performed at 550° C. for 3 hours, and then dehydrogenation of butene was performed at a reaction temperature of 600° C. under normal pressure. As a raw material, 2-butene (a mixture of trans-2-butene and cis-2-butene) was used, and the raw-material gas composition was determined to be 2-butene:nitrogen:water=1.5:5.3:3.2 (molar ratio). WHSV was determined to be 1.5 h$^{-1}$ in Examples 1 to 3 and Comparative Examples 1 to 2, and 1.0 h$^{-1}$ in Examples 4 to 5.

A product gas was collected 0.5 hours, 1 hour, and 2 hours after the start of the reaction, respectively, and analyzed by gas chromatography (Agilent Technologies GC-6850, FID+TCD detector) to find the butene conversion rate and the butadiene yield at each reaction time. Furthermore, the amount of change per unit time in the butene conversion rate and the butadiene, yield were found as the degrees of deterioration. The obtained results are shown in Table 1.

TABLE 1

| Dehydrogenation catalyst | | 0.5 h | 1 h | 2 h | Degree of deterioration (%/h) |
|---|---|---|---|---|---|
| A-1 | Butene conversion rate | 22.9 | 23.2 | 22.0 | 0.60 |
| | Butadiene yield | 20.6 | 20.9 | 19.6 | 0.67 |
| A-2 | Butene conversion rate | 22.7 | 22.5 | 21.0 | 1.1 |
| | Butadiene yield | 20.3 | 20.2 | 18.9 | 0.93 |
| A-3 | Butene conversion rate | — | 41.9 | 40.0 | 1.9 |
| | Butadiene yield | — | 24.1 | 24.2 | 0.1 |
| A-4 | Butene conversion rate | — | 10.0 | 8.5 | 1.5 |
| | Butadiene yield | — | 8.1 | 6.8 | 1.3 |
| A-5 | Butene conversion rate | 33.6 | 32.5 | 32.8 | 0.53 |
| | Butadiene yield | 27.6 | 27.5 | 27.8 | 0.13 |
| B-1 | Butene conversion rate | 30.8 | 27.0 | 20.0 | 7.2 |
| | Butadiene yield | 26.7 | 22.6 | 17.9 | 5.9 |
| B-2 | Butene conversion rate | 17.9 | 14.9 | 13.5 | 2.9 |
| | Butadiene yield | 15.5 | 13.0 | 11.9 | 2.4 |

As shown in Table 1, the dehydrogenation catalysts A-1 to A-5 obtained in Examples 1 to 5 were confirmed to have suppressed deterioration thereof and good reactivity over a long period of time. On the other hand, the dehydrogenation catalyst B-1 obtained in Comparative Example 1 exerted high initial activity, but was quickly deteriorated and was unable to maintain reactivity for a long time. Moreover, the dehydrogenation catalyst B-2 obtained in Comparative Example 2 exerted low initial activity, and was deteriorated quickly.

<Dehydrogenation 2>

Dehydrogenation was performed by the following method using the dehydrogenation catalysts obtained in Examples 6 to 10 and Comparative Example 3.

A flow-type reactor having an inner diameter of 10 mmφ was filled with 1.00 g of each dehydrogenation catalyst, hydrogen reduction was performed at 550° C. for 3 hours, and then dehydrogenation of butane was performed at a reaction temperature of 550° C. under normal pressure. As a raw material, n-butane was used, the pigment gas composition was determined to be n-butane:nitrogen:water=1.0:5.3:3.2 (molar ratio), and WHSV was determined to be 1.0 h$^{-1}$.

A product gas was collected 1 hour, 2 hours, and 4 hours after the start of the reaction, respectively, analyzed by gas chromatography (Agilent Technologies GC-6850, FID+TCD detector), and then the butane conversion rate and the unsaturated hydrocarbon (butene+butadiene) yield at each reaction time were found. The obtained results are shown in Table 2.

TABLE 2

| Dehydrogenation catalyst | | 1 h | 2 h | 4 h |
|---|---|---|---|---|
| A-6 | Butane conversion rate | 63 | 57 | 50 |
| | Unsaturated hydrocarbon yield | 58 | 53 | 46 |
| A-7 | Butane conversion rate | 49 | 45 | 41 |
| | Unsaturated hydrocarbon yield | 45 | 41 | 38 |
| A-8 | Butane conversion rate | 67 | 62 | 50 |
| | Unsaturated hydrocarbon yield | 62 | 57 | 47 |
| A-9 | Butane conversion rate | 38 | 35 | 33 |
| | Unsaturated hydrocarbon yield | 35 | 32 | 30 |
| A-10 | Butane conversion rate | 48 | 45 | 43 |
| | Unsaturated hydrocarbon yield | 45 | 41 | 38 |
| B-3 | Butane conversion rate | 41 | 35 | 31 |
| | Unsaturated hydrocarbon yield | 37 | 31 | 28 |

<Dehydrogenation 3>

Dehydrogenation was performed by the following method using the dehydrogenation catalysts obtained in Examples 5 and 8.

A flow-type reactor having an inner diameter of 10 mmφ was filled with 1.20 g of the dehydrogenation catalyst A-8 and 0.80 g of the dehydrogenation catalyst A-5, so that the catalysts were layered in order of A-8 and A-5, and then hydrogen reduction was performed at 550° C. for 3 hours. Dehydrogenation was performed at a reaction temperature of 550° C. at the position for filling with the dehydrogenation catalyst A-8 and at a reaction temperature of 600° C. at the position for filling with the dehydrogenation catalyst A-5 under normal pressure. The raw material used herein was n-butane, the raw-material gas composition was determined to be n-butane:nitrogen:water=1.0:5.3:3.2 (molar ratio), WHSV was determined to be 0.67 for the catalyst A-8, and 1.0 h$^{-1}$ for the catalyst A-5.

A product gas was collected 1 hour, 3 hours, 5 hours, 11 hours, and 14 hours after the start of the reaction, respectively, and then analyzed by gas chromatography (Agilent Technologies GC-6850, FID+TCD detectors) to find the butane conversion rate and the unsaturated hydrocarbon (butene+butadiene) yield, and the butadiene yield at each reaction time. The obtained results are shown in Table 3.

TABLE 3

| Dehydrogenation catalyst | | 1 h | 3 h | 5 h | 11 h | 14 h |
|---|---|---|---|---|---|---|
| A-5/A-8 | Butane conversion rate | 76 | 71 | 67 | 56 | 51 |
| | Unsaturated hydrocarbon yield | 67 | 64 | 60 | 50 | 46 |
| | Butadiene yield | 17 | 17 | 16 | 14 | 14 |

The invention claimed is:

1. A method for producing a dehydrogenation catalyst, comprising:
    a step of impregnating a carrier with a first solution having a tin source dissolved therein, so as to have tin supported on the carrier; and
    a step of impregnating the carrier with a second solution having an active metal source dissolved therein, so as to have the active metal supported on the carrier, wherein
        the tin source is at least one selected from the group consisting of sodium stannate and potassium stannate, and
        the active metal source has at least one active metal selected from the group consisting of platinum, ruthenium and iridium, and has no chlorine atom, and the amount of tin supported in the dehydrogenation catalyst is 7 mass % or more.

2. The production method according to claim 1, wherein the first solution is an aqueous solution.

3. A method for producing an unsaturated hydrocarbon, comprising a step of performing dehydrogenation of an alkane utilizing a dehydrogenation catalyst produced by the production method according to claim 1, so as to obtain at least one unsaturated hydrocarbon selected from the group consisting of an olefin and a conjugated diene.

4. A method for producing a conjugated diene, comprising a step of performing dehydrogenation of an olefin utilizing a dehydrogenation catalyst produced by the production method according to claim 1, so as to obtain a conjugated diene.

* * * * *